US00PP32393P2

(12) United States Plant Patent
Wood

(10) Patent No.: US PP32,393 P2
(45) Date of Patent: Oct. 27, 2020

(54) JUNIPER PLANT NAMED 'SMNJCB'

(50) Latin Name: *Juniperus communis*
Varietal Denomination: SMNJCB

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/602,668

(22) Filed: Nov. 18, 2019

(51) Int. Cl.
*A01H 5/00* (2018.01)

(52) U.S. Cl.
USPC ..... Plt./214

(58) Field of Classification Search
USPC ..... Plt./214
CPC ..... A01H 5/00
See application file for complete search history.

*Primary Examiner* — Annette H Para
(74) *Attorney, Agent, or Firm* — C. A. Whealy

(57) ABSTRACT

A new and distinct cultivar of Juniper plant named 'SMNJCB', characterized by its relatively compact, outwardly spreading to arching and mounding plant form; freely branching habit requiring minimal pruning; dense and bushy appearance; green-colored leaves that maintain their color throughout the seasons; and good landscape performance and hardiness.

2 Drawing Sheets

Figure 1:
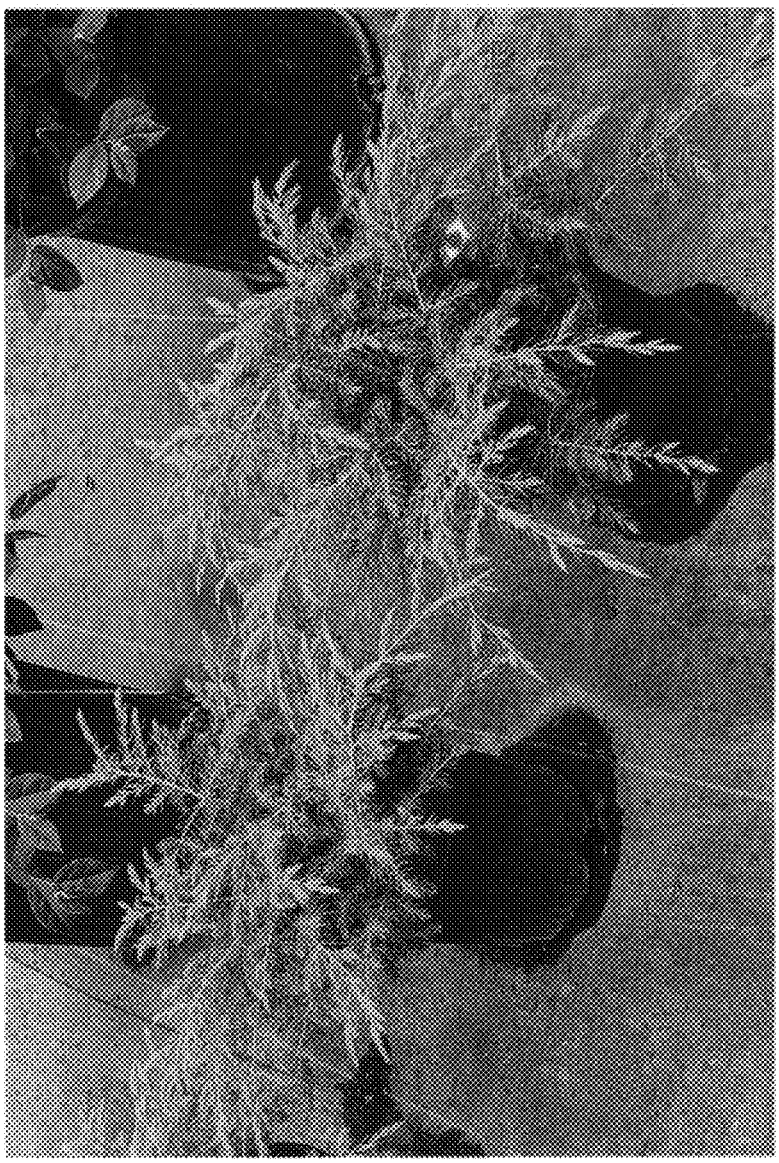

Botanical designation: *Juniperus communis*.
Cultivar denomination: 'SMNJCB'.

BACKGROUND OF THE INVENTION

The present Invention relates to a new and distinct cultivar of Juniper plant, botanically known as *Juniperus communis*, and hereinafter referred to by the name 'SMNJCB'.

The new Juniper plant is a product of a planned breeding program conducted by the Inventor in Grand Haven, Mich. The objective of the breeding program was to create new Juniper plants with unique and attractive plant forms.

The new Juniper plant originated from an open-pollination in 2005 in Grand Haven, Mich. of an unnamed selection *Juniperus communis*, not patented, as the female, or seed, parent with an unknown selection of *Juniperus communis* as the male, or pollen, parent. The new Juniper plant was discovered and selected by the Inventor as a single plant from within the progeny of the stated open-pollination in a controlled environment in Grand Haven, Mich. in 2009.

Asexual reproduction of the new Juniper plant by softwood stem cuttings taken in a controlled environment in Grand Haven, Mich. since 2009 has shown that the unique features of this new Juniper plant are stable and reproduced true to type in successive generations.

SUMMARY OF THE INVENTION

Plants of the new Juniper have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'SMNJCB'. These characteristics in combination distinguish 'SMNJCB' as a new and distinct Juniper plant:

1. Relatively compact, outwardly spreading to arching and mounding plant form.
2. Freely branching habit requiring minimal pruning; dense and bushy appearance.
3. Green-colored leaves that maintain their color throughout the seasons.
4. Good landscape performance and hardiness.

Plants of the new Juniper can be compared to plants of the female parent selection in plant size as plants of the new Juniper are more compact than plants of the female parent selection.

Plants of the new Juniper can be compared to plants of *Juniperus communis* 'Blueberry Delight', not patented. Plants of the new Juniper differ primarily from plants of 'Blueberry Delight' in the following characteristics:

1. Plants of the new Juniper are more compact than plants of 'Blueberry Delight'.
2. Leaves of plants of the new Juniper are green in color whereas leaves of plants of 'Blueberry Delight' are bluish green in color.

BRIEF DESCRIPTION OF THE PHOTOGRAPHS

The accompanying colored photographs illustrate the overall appearance of the new Juniper plant showing the colors as true as it is reasonably possible to obtain in colored reproductions of this type. Colors in the photographs may differ slightly from the color values cited in the detailed botanical description which accurately describe the colors of the new Juniper plant.

The photograph on the first sheet (FIG. 1 of 2) is a side perspective view of typical plants of 'SMNJCB' grown in containers; plants used in the photograph are three years old.

Figure 2:
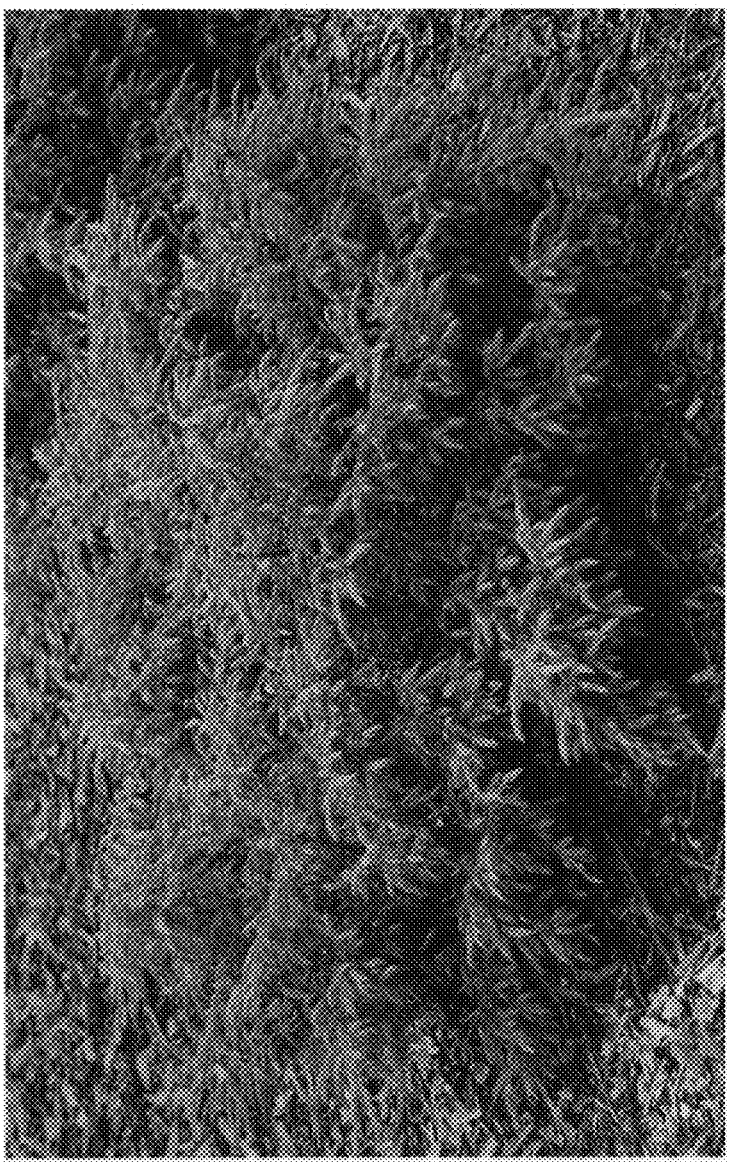

The photograph on the second sheet (FIG. 2 of 2) is a side perspective view of a typical plant of 'SMNJCB' grown in an outdoor nursery; plant used in the photograph is five years old.

DETAILED BOTANICAL DESCRIPTION

Plants used for the following observations and measurements were grown during the summer in one-gallon containers in a polyethylene-covered greenhouse in Grand Haven, Mich. Plants were grown under cultural practices typical of commercial Juniper plant production. During the production of the plants, day temperatures ranged from 18° C. to 27° C. and night temperatures ranged from 5° C. to 10° C. Plants were two years old when the description was taken. In the following description, color references are made to The Royal Horticultural Society Colour Chart, 2015 Edition, except where general terms of ordinary dictionary significance are used.

Botanical classification: *Juniperus communis* 'SMNJCB'.

Parentage:

*Female, or seed, parent*.—Unnamed selection of *Juniperus communis*, not patented.

*Male, or pollen, parent*.—Unknown selection of *Juniperus communis*, not patented.

Propagation:

*Type*.—By softwood stem cuttings.

*Time to initiate roots*.—About three months at temperatures about 18° C. to 27° C.

*Time to produce a rooted cutting*.—About 200 days at temperatures about 18° C. to 27° C.

*Root description*.—Thick to thin, fibrous; typically brown and white in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Perennial evergreen shrub; relatively compact, outwardly spreading to arching and mounding plant form; vigorous growth habit and moderate growth rate.

*Branching habit*.—Freely branching habit requiring minimal pruning; dense and bushy appearance; about 15 to 20 lateral branches developing per plant.

*Plant height*.—About 18 cm.

*Plant diameter*.—About 65 cm.

*Lateral branch description*.—Length: About 32 cm. Diameter: About 2 mm. Internode length: About 1 cm to 2 cm. Strength: Strong, flexible. Aspect: About 45° from vertical. Texture: Rounded to four-sided, glabrous. Color, developing: Close to N144A. Color, mature: Close to 177A.

*Leaf description*.—Arrangement: Whorled; simple; sessile. Length: About 1.1 cm. Width: About 1 mm. Shape: Acicular. Apex: Acute. Base: Truncate. Margin: Entire. Texture, upper and lower surfaces: Smooth, glabrous. Venation pattern: Parallel. Color: Developing leaves, upper surface: Close to 143A; midrib, close to 157A. Developing leaves, lower surface: Close to 143A. Fully expanded leaves, upper surface: Close to 141A; midrib, close to 157A; leaf color is maintained throughout the seasons. Fully expanded leaves, lower surface: Close to 141A; venation, close to 141A; leaf color is maintained throughout the seasons.

*Cone description*.—Quantity: About 20 cones develop per branch and numerous cones develop per plant. Length: About 7 mm. Diameter: About 4 mm. Texture: Smooth, waxy sheen. Color: Close to N144A.

Pathogen & pest resistance: To date, plants of the new Juniper have not been observed to be resistant to pathogens or pests common to Juniper plants.

Landscape performance: Plants of the new Juniper have been observed to have good landscape performance and to be tolerant temperatures ranging from about −32° C. to about 36° C.

It is claimed:

1. A new and distinct Juniper plant named 'SMNJCB' as illustrated and described.

* * * * *